(12) United States Patent
Sun (10) Patent No.: US 9,816,952 B2
(45) Date of Patent: Nov. 14, 2017

(54) METHOD AND APPARATUS FOR IMPLEMENTING MATERIAL THERMAL PROPERTY MEASUREMENT BY FLASH THERMAL IMAGING

(71) Applicant: UChicago Argonne, LLC, Chicago, IL (US)

(72) Inventor: Jiangang Sun, Westmont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 387 days.

(21) Appl. No.: 14/632,201

(22) Filed: Feb. 26, 2015

(65) Prior Publication Data
US 2016/0252399 A1 Sep. 1, 2016

(51) Int. Cl.
*G01N 25/18* (2006.01)
(52) U.S. Cl.
CPC .................................. *G01N 25/18* (2013.01)
(58) Field of Classification Search
CPC .............................................. G01J 2005/0077
See application file for complete search history.

(56) References Cited

U.S. PATENT DOCUMENTS

| 7,365,330 B1* | 4/2008 | Sun | A61B 5/015 |
| | | | 250/341.6 |
| 7,538,938 B2* | 5/2009 | Sun | G02B 5/208 |
| | | | 359/359 |
| 7,769,201 B2 | 8/2010 | Sun | |
| 8,465,200 B2 | 6/2013 | Sun | |

\* cited by examiner

*Primary Examiner* — Yu-Hsi D Sun
(74) *Attorney, Agent, or Firm* — Joan Pennington (57) ABSTRACT

A method and apparatus are provided for implementing measurement of material thermal properties including measurement of thermal effusivity of a coating and/or film or a bulk material of uniform property. The test apparatus includes an infrared camera, a data acquisition and processing computer coupled to the infrared camera for acquiring and processing thermal image data, a flash lamp providing an input of heat onto the surface of a two-layer sample with an enhanced optical filter covering the flash lamp attenuating an entire infrared wavelength range with a series of thermal images is taken of the surface of the two-layer sample.

14 Claims, 5 Drawing Sheets

METHOD AND APPARATUS FOR IMPLEMENTING MATERIAL THERMAL PROPERTY MEASUREMENT BY FLASH THERMAL IMAGING

CONTRACTUAL ORIGIN OF THE INVENTION

The United States Government has rights in this invention pursuant to Contract No. DE-AC02-06CH11357 between the United States Government and UChicago Argonne, LLC representing Argonne National Laboratory.

FIELD OF THE INVENTION

The present invention relates generally to the measurement of material thermal properties by using a flash infrared thermal imaging apparatus and method, and more particularly, relates to a method and apparatus for implementing the measurement of thermal properties including thermal effusivity of a coating and/or film and a bulk material of uniform property.

DESCRIPTION OF THE RELATED ART

Thermal properties are needed in almost all material applications involved with temperature. There are two primary thermal properties: thermal conductivity k and specific heat capacity c (at constant pressure). Thermal conductivity k is related to the ability of a material to transport thermal energy, and specific heat c is for storing energy. The volumetric heat capacity (or called heat capacity here for simplicity) $\rho c$, where $\rho$ is material density, is usually more relevant than specific heat in applications. These two thermal properties k and $\rho c$ may be converted into another two parameters: thermal effusivity e ($=(\rho ck)^{1/2}$) and thermal diffusivity $\alpha$ ($=k/\rho c$). Thermal effusivity e is related to the energy or heat exchange between materials and thermal diffusivity $\alpha$ to the speed of thermal diffusion. It is apparent that if any two of these four parameters are known, the other two parameters can be derived from them. A typical testing method may determine one or two such parameters.

As new materials are being routinely developed, there is always a need for their thermal property measurement. This is especially true for coatings, because an accurate and nondestructive testing method for a wide range of coating materials has not been available. Thermal property measurement may also be used to monitor material processing conditions, for example, mixing of two fluids of different thermal properties and monitoring moisture content in a material drying process. Because of their importance, numerous testing methods have been developed to measure these thermal properties. A traditional standard testing method for conductivity measurement uses a steady-state heat flux and temperature measurement apparatus; steady-state methods are normally time consuming. Many current measurements utilize the transient laser flash method that is fast. Laser flash determines the thermal diffusivity that can be converted into conductivity when the material's heat capacity is known. On the other hand, the standard testing method for specific heat is the differential scanning calorimetry (DSC). Commercial turn-key instruments for both laser flash and DSC methods are widely available.

Beside bulk materials, another important engineering material is coating or film. Although some current methods may be configured for coating property measurement (e.g., laser flash), they usually are of limited accuracy and not done in a nondestructive way. Other testing methods specifically developed for coatings are also of limited accuracy. Because of the importance of coating materials in many energy-related and transportation-related industrial applications, a nondestructive method for detection of coating property is necessary.

Besides the commercial laser flash method that uses flash heating, other testing methods for thermal properties measurement employ modulated thermal excitation and detection. Modulation or lock-in methods can easily detect the signal phase change that is related to material properties. Although such methods are reported to provide measurement accuracy, most however were only evaluated for limited material property ranges. On the other hand, the laser flash method can normally achieve a measurement accuracy of <2% absolute errors.

U.S. Pat. No. 7,769,201, by the present inventor Jiangang Sun entitled "METHOD FOR ANALYZING MULTILAYER MATERIALS FROM ONE-SIDED PULSED THERMAL IMAGING" discloses a method for multilayer materials that was developed to determine multiple material parameters including conductivity, optical transmission, and thickness and/or crack depth for each layer.

U.S. Pat. No. 7,538,938 issued May 26, 2009 to the present inventor Jiangang Sun entitled "OPTICAL FILTER FOR FLASH LAMPS IN PULSED THERMAL IMAGING" discloses an optical filter that is provided for flash lamps used in pulsed thermal imaging. The optical filter covers a flash lamp and allows visible wavelength to penetrate while blocking infrared wavelengths that are sensitive to an infrared camera. The filter substantially eliminates the infrared radiation from flash lamps to allow for accurate detection of surface temperature during pulsed thermal imaging tests. The filter is made from a borosilicate optical material. The filter allows for the complete data obtained in a thermal imaging test to be usable and accurate, without errors introduced by flash reflection effect and residual heating effect.

U.S. Pat. No. 7,365,330 issued Apr. 29, 2008 to the present inventor Jiangang Sun entitled "METHOD FOR THERMAL TOMOGRAPHY OF THERMAL EFFUSIVITY FROM PULSED THERMAL IMAGING" discloses a computer-implemented method for automated thermal computed tomography that includes providing an input of heat, for example, with a flash lamp, onto the surface of a sample. The amount of heat and the temperature rise necessary are dependent on the thermal conductivity and the thickness of the sample being inspected. An infrared camera takes a rapid series of thermal images of the surface of the article, at a selected rate, which can vary from 100 to 2000 frames per second. Each infrared frame tracks the thermal energy as it passes from the surface through the material. Once the infrared data is collected, a data acquisition and control computer processes the collected infrared data to form a three-dimensional (3D) thermal effusivity image.

While the above-identified U.S. Patents have provided significant improvements over other known arrangements, it is desirable to provide an enhanced method and apparatus for implementing measurement of material thermal properties including measurement of thermal effusivity of a coating and/or film or a bulk material of uniform property.

SUMMARY OF THE INVENTION

Principal aspects of the present invention are to provide a method and apparatus for implementing measurement of material thermal properties including measurement of thermal effusivity of a coating and/or film or a bulk material of uniform property. Other important aspects of the present invention are to provide such method and apparatus substantially without negative effect and that overcome some of the disadvantages of prior art arrangements.

In brief, a method and apparatus are provided for implementing measurement of material thermal properties including measurement of thermal effusivity of a coating and/or film or a bulk material of uniform property. The test apparatus includes an infrared camera, a data acquisition and processing computer coupled to the infrared camera for acquiring and processing thermal image data, a flash lamp providing an input of heat onto the surface of a two-layer sample with an enhanced optical filter covering the flash lamp attenuating an entire infrared wavelength range with a series of thermal images is taken of the surface of the two-layer sample. A measurement solution determines material thermal properties using the following equations $$T_f(t) = Q \cdot f_1(e_1^2 t) \cdot f_3\left(\frac{e_1}{e_2}, \frac{\alpha_1}{L_1^2}, t\right), \quad (1)$$

$$T_f(t) = \frac{Q}{\rho_1 c_1 L_1 + \rho_2 c_2 L_2} \cdot f_4\left(\frac{e_1}{e_2}, \frac{\alpha_1}{L_1^2}, \frac{\alpha_2}{L_2^2}, t\right), \quad (2)$$

where $T_f(t)$ represents a front surface temperature, where t is time and Q is the total amount of absorbed energy (heat) on surface for the two-layer sample of materials of uniform properties with an instantaneous heat impulse for the cases of a semi-infinite and a finite substrate thickness material, respectively; where L represents sample thickness, e represents thermal effusivity and ρc represents heat capacity; where the subscripts 1 and 2 denote the first-layer or shallow layer material and a second-layer or deep layer material, respectively.

In accordance with features of the invention, the measurement method is based on a two-layer material model under flash thermal imaging test condition In accordance with features of the invention, the test apparatus is simple to setup and operate, can be operated in elevated temperatures, can test solid and liquid materials, and can obtain two-dimensional property distribution data. Because of the inherent high accuracy and apparatus flexibility, the method may be used as a standard testing method for coating and bulk materials.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

In the following detailed description of embodiments of the invention, reference is made to the accompanying drawings, which illustrate example embodiments by which the invention may be practiced. It is to be understood that other embodiments may be utilized and structural changes may be made without departing from the scope of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

In accordance with features of the invention, a method and apparatus for implementing the measurement of material thermal properties by using a flash infrared thermal imaging method are provided. In particular, the method can accurately measure the thermal effusivity of a coating/film or a bulk material of uniform property. When the bulk material is a plate, it also measures the thermal diffusivity of the plate with known plate thickness (or vice versa).

In accordance with features of the invention, the invented method is based on a two-layer material configuration under flash thermal imaging test condition. The test apparatus including sample preparation is simple to setup and operate, can be operated at elevated temperatures, can test solid and liquid materials, and can obtain two-dimensional property distribution data. Because of the inherent high accuracy and apparatus flexibility, this method may be used as a standard testing method for coating and bulk materials.

In accordance with features of the invention, the invented method enables (1) measuring thermal effusivity at <2% absolute errors for coatings or films without the need of any input coating/film material parameters; (2) measuring thermal effusivity at <2% absolute errors for a bulk material without the need of any input material parameters; and (3), when combined with (2), measure thermal diffusivity of a plate bulk material with the input of plate thickness. The combination of (2) and (3) can therefore determine the two primary thermal properties, thermal conductivity and heat capacity. In addition for average property measurement, the measuring apparatus of FIG. 1 also allows for the determination of two-dimensional distributions of these thermal properties.

In principle a test method relies on two steps to determine material thermal properties: first a theoretical solution for the exact material configuration and test conditions is obtained which contains the unknown material properties; secondly the theoretical solution is required to match with test data (e.g. surface temperature variations) and the best match produces the needed material thermal properties. The second step is usually achieved by a regression algorithm, such as the least-square fitting used in this invented method. As a result, the capability of a test method is dependent upon the presence of unique features in the theory to extract material properties from a specific material/test configuration. To illustrate the principles of various methods, including the laser flash method and this invented method, we list some fundamental solutions of the one-dimensional governing heat transfer equation for one- and two-layer materials when applied with an instantaneous thermal excitation on the sample's front surface. For actual thermal excitation types used in various methods, e.g., steady, pulsed, or modulated, the formulations used in those methods can be obtained simply by convolution of the fundamental solutions with the excitation intensity function. The fundamental solutions listed below, however, allow for a direct identification of the independent material parameters that may be determined by these methods. In all following solutions, the initial temperature of the materials is assumed to be zero; therefore all temperatures represent differential temperatures.

For a semi-infinite bulk material of uniform material properties, the solution of its front surface temperature $T_f$ after applying an instantaneous heat impulse is represented by:

$$T_f(t) = \frac{Q}{e\sqrt{\pi t}} = Q \cdot f_1(e^2 t), \tag{a}$$

where t is time and Q is the total amount of absorbed energy (heat) on surface. It is obvious that the thermal effusivity e could be determined from temperature measurement if Q was known; however, Q is usually difficult to be measured accurately. On the other hand, unlike other theories listed below, the function $f_1$ defined in Eq. (a) does not have any characteristic feature to allow for a direct extraction of the effusivity e value.

For a finite-thickness (plate) bulk material of uniform property, the solution of its back surface temperature $T_b$ after applying an instantaneous heat impulse on front surface is expressed in the following functional form:

$$T_b(t) = \frac{Q}{\rho c L} \cdot f_2\left(\frac{\alpha t}{L^2}\right), \tag{b}$$

$$f_2 = 1 + 2\sum_{n=1}^{\infty} (-1)^n \exp\left(-\frac{n^2\pi^2}{L^2}\alpha t\right), \tag{ba}$$

where L is sample thickness which is usually known. The derivative of the function $f_2$ has a characteristic peak with a constant magnitude—this feature allows for a direction extraction of $\alpha/L^2$ when the peak location t is determined from $f_2$. In practice, however, it is more convenient to measure a so-called half-rise time as employed in the standard laser flash method. The laser flash method may also determine the heat capacity $\rho c$ after the applied heat Q is measured from a separate calibration test using a reference sample.

In accordance with features of the invention, the invented method for two-layer materials of uniform properties, the theoretical solutions of the front surface temperature $T_f$ after being applied with an instantaneous heat impulse for the cases of a semi-infinite and a finite substrate thickness material are expressed respectively in the following two functional forms:

$$T_f(t) = Q \cdot f_1(e_1^2 t) \cdot f_3\left(\frac{e_1}{e_2}, \frac{\alpha_1}{L_1^2}, t\right), \tag{1}$$

$$f_3 = 1 + 2\sum_{n=1}^{\infty} \left(\frac{e_{12}-1}{e_{12}+1}\right)^n \exp\left(-\frac{n^2 L_1^2}{\alpha_1 t}\right), \tag{1a}$$

$$T_f(t) = \frac{Q}{\rho_1 c_1 L_1 + \rho_2 c_2 L_2} \cdot f_4\left(\frac{e_1}{e_2}, \frac{\alpha_1}{L_1^2}, \frac{\alpha_2}{L_2^2}, t\right), \tag{2}$$

$$f_4 = 1 + \tag{2a}$$

$$2\frac{x_1\omega_1 + x_2\omega_2}{x_1 + x_2}\sum_{K=1}^{\infty} \frac{x_1\cos(\omega_1\gamma_K) + x_2\cos(\omega_2\gamma_K)}{x_1\omega_1\cos(\omega_1\gamma_K) + x_2\omega_2\cos(\omega_2\gamma_K)}\exp\left(-\frac{\gamma_K^2 t}{\eta_2^2}\right),$$

where $\gamma_K$ is the K-th positive root of the following equation, $$x_1 \sin(\omega_1\gamma) + x_2 \sin(\omega_2\gamma) = 0, \tag{2b}$$

x and $\omega$ are defined as, $$x_i = e_{12} - (-1)^i, e_i = \sqrt{k_i \rho_i c_i}, i=1,2 \tag{2c}$$

$$\omega_i = \eta_{12} - (-1)^i, \eta_i = L_i/\sqrt{\alpha_i}, i=1,2 \tag{2d}$$

$$e_{12} = e_1/e_2, \eta_{12} = \eta_1/\eta_2. \tag{2e}$$

where the subscripts 1 and 2 denote the first-layer (shallower) and second-layer (deeper) materials, respectively. Equation (1) may be considered as a subset of Eq. (2), because in principle Eq. (2) should approach to Eq. (1) when the second-layer thickness $L_2$ goes to infinity. Equations (1) and (2) are the foundation of this invented method.

Figure 1:
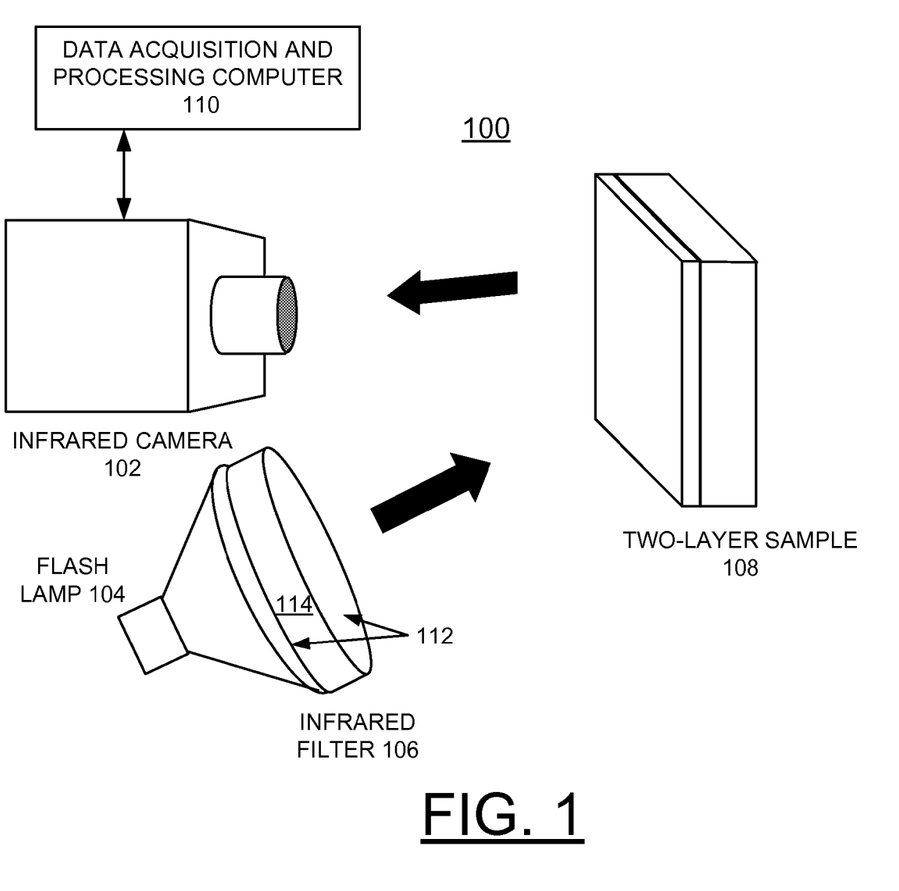
FIG. 1 schematically illustrates not to scale an example apparatus for implementing measurement of material thermal properties including measurement of thermal effusivity of a coating and/or film or a bulk material of uniform property in accordance with a preferred embodiment.

Having reference now to the drawings, in FIG. 1, there is shown an example undulator including example apparatus for implementing measurement of material thermal properties including measurement of thermal effusivity of a coating and/or film or a bulk material of uniform property generally designated by the reference character 100 in accordance with a preferred embodiment. The test apparatus 100 includes an infrared camera 102, a flash lamp 104 with an enhanced optical filter 106 covering the flash lamp 104 providing an input of heat onto the surface of a two-layer sample 108, and a data acquisition and processing computer 110 coupled to the infrared camera 102 for acquiring and processing thermal image data.

The enhanced optical filter 106 covering the flash lamp 104 attenuating an entire infrared wavelength range with a series of thermal images is taken of the surface of the two-layer sample. The enhanced optical filter 106 eliminates all infrared light radiated by the flash lamp 104 from reaching the sample surface to cause measurement errors. In the above-identified U.S. Pat. No. 7,538,938, the filter is made from borosilicate glasses. In the enhanced new infrared filter 106 is constructed by a pair of glass plates 112 enclosing a water layer 114. Water is efficient to attenuate infrared lights from a typical flash lamp that emits optical energy similar to the blackbody radiation at a temperature of 5600K.

By comparing the normalized blackbody radiation spectrum emitted at a temperature of 5600K before and after passing through a 3-mm-thick water layer 114 as well as the normalized blackbody radiation spectrum from a test sample at room temperature (300K) that is imaged by infrared camera 110, it has been determined that the water layer 114 attenuates the optical emissions from the flash lamp 104 by more than 26 orders of magnitudes in the entire infrared 2.5-10 micron wavelength range. As a result, the flash radiation does not interfere with the infrared detection at the sample temperature (~300K or higher), which ensures the accuracy of the experimental data to be used for material thermal property determination.

In accordance with features of the invention, the foundation of this invented method becomes evident from a detailed parametric analysis for the two-layer theory in Eqs. (1) and (2).

Thermal Effusivity Measurement for Coating

For a two-layer, coating/substrate system, the coating surface temperature measured under flash thermal imaging follows Eq. (2).

Figure 2:
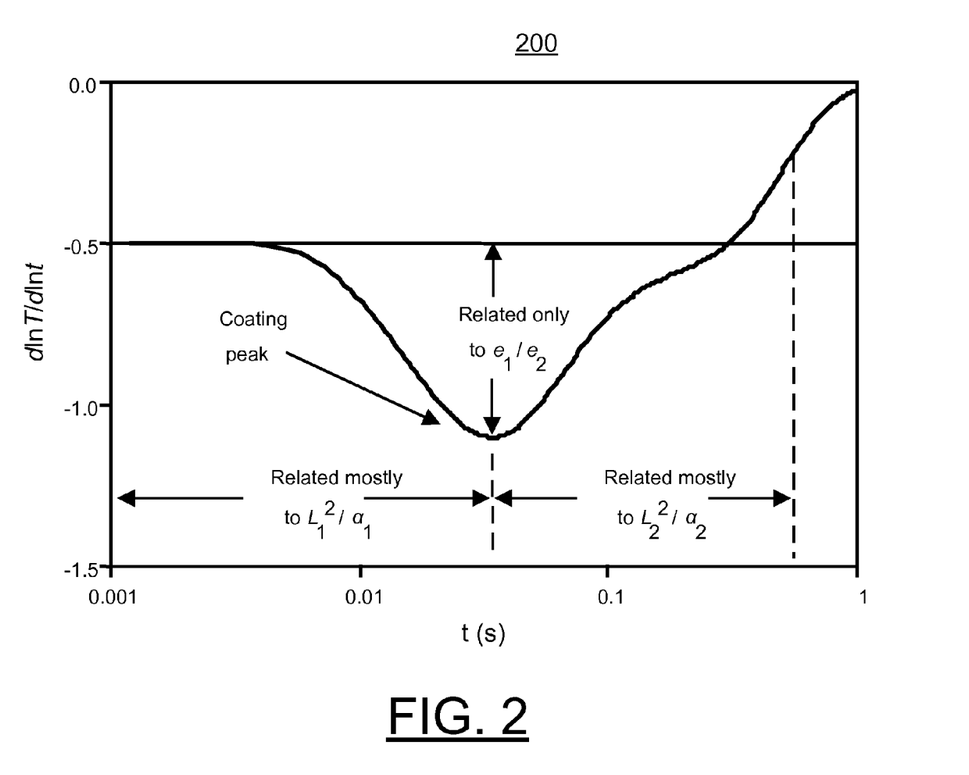
FIG. 2 is a chart illustrating an example front-surface temperature slope as a function of time for a typical opaque coating/substrate measured by the system of FIG. 1 in accordance with preferred embodiments.

FIG. 2 is a plot of the front-surface temperature slope as a function of time for a typical opaque coating/substrate system generally designated by the reference character 200. When substrate properties ($e_2$, $\alpha_2$) are known (which is normally the case), it was demonstrated that two coating parameters, effusivity $e_1$ and parameter $L_1^2/\alpha_1$, may be determined directly from the shape of the curve in FIG. 2 that illustrates a typical logarithmic surface-temperature slope (d ln T/d ln t) curve based on Eq. (2) (note that this surface temperature is measured by flash thermal imaging tests). This curve has a characteristic (negative) coating peak that is due to the difference of thermal effusivities between the coating and the substrate. The temperature slope becomes zero at longer times for the condition of finite substrate thickness $L_2$ (Eq. (2)) but remains to be at $-0.5$ indefinitely for the condition of semi-infinite substrate (Eq. (1)).

Because $e_1$ and $L_1^2/\alpha_1$ are independent from each other, measured thermal effusivity $e_1$ is not affected by coating thickness or diffusivity variations. This unique feature allows for the absolute measurement of the coating thermal effusivity without the need to know any information about the coating, while such capability has not been demonstrated by other methods. Because thermal effusivity is unique for a coating material, it can be interpreted as an indicator of the quality of the coating. This coating effusivity measurement can achieve an accuracy of <2% absolute errors as demonstrated in the next section.

Thermal Effusivity Measurement for Bulk Material

When the bulk material is a plate with a thickness $L_2$, its thermal diffusivity $\alpha_2$ may also be derived directly from the thermal imaging data where the parameter $L_2^2/\alpha_2$ is determined from the time period after the negative coating peak.

As described above, FIG. 2 also indicates that if the coating thermal effusivity $e_1$ is known, we can also measure/predict the substrate effusivity $e_2$ (because $e_1/e_2$ is an independent parameter in Eqs. (1) and (2)). This therefore may serve as a new method for measuring the thermal effusivity of an unknown bulk material. The question then becomes how to find a film material that has a constant thermal effusivity and can be reliably bonded to the bulk test material. One such material has been found: the commercial black electric tape commonly used in household electric works (although many others may also be suitable). The electric tape consists of a polymer film and an adhesive layer with a total thickness of ~0.2 mm. It has several advantages for thermal imaging application: it is black with high thermal emissivity so is very efficient for heat absorption and emission; its thickness is adequate for short test duration while not requiring very fast imaging speed obtainable only with high-end infrared cameras; and it is easily bonded well with all smooth solid materials and with liquid materials (possibly also with powder materials although powder was not evaluated). One problem with the electric tape is that it is not completely opaque; this effect however has been accounted for by the method (in which the attenuation coefficient was explicitly modeled and calculated). There were also concerns that the tape effusivity may vary due to material nonuniformity (these tapes are not made as a test standard) or thickness change (e.g., when stretched) that is difficult to determine. These concerns were dismissed because the consistency of the measurement results as shown in FIG. 3.

Figure 3:
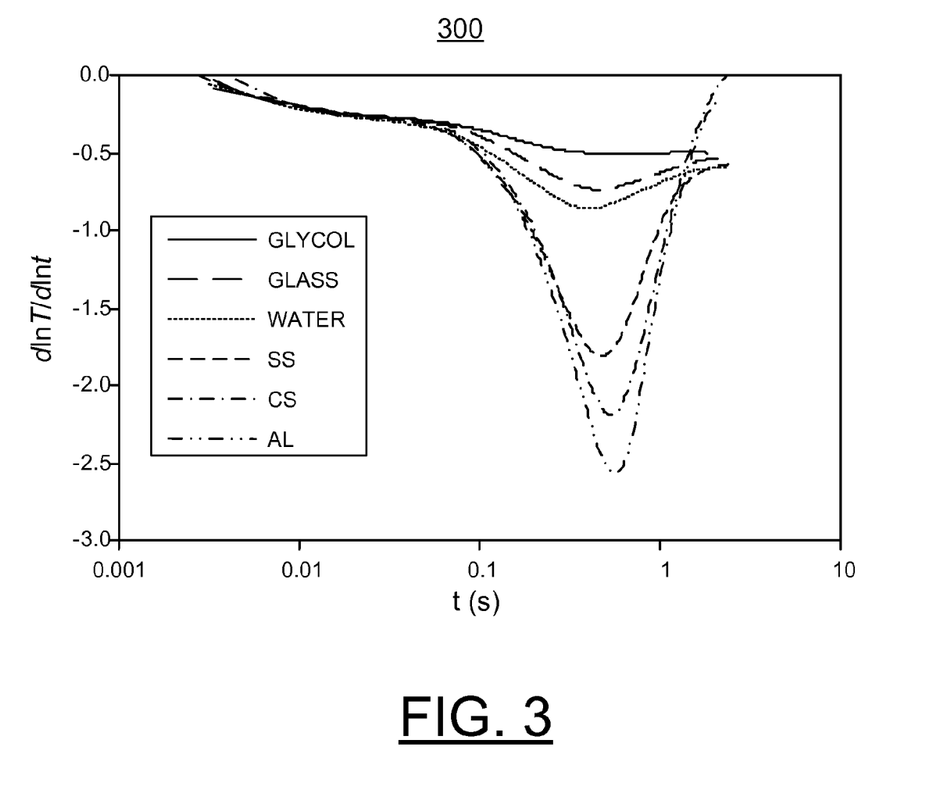
FIG. 3 is a chart illustrating measured temperature slope curves for example materials in accordance with preferred embodiment.

FIG. 3 shows the measured temperature slope curves for these materials generally designated by the reference character 300. The thermal effusivity of the electric tape was determined by using the water as the calibration material (i.e., the substrate); it was then used to measure the thermal effusivity of all other materials. FIG. 3 illustrates materials characteristics in the temperature slope curve, namely the peak magnitude and the time lengths at the two sides of the coating peak. As shown in FIG. 2, these characteristics can be used to determine the three material parameters in Eq. (2): $e_1/e_2$, $L_1^2/\alpha_1$, and $L_2^2/\alpha_2$. It can be shown that the thermal effusivity ratio $e_1/e_2$ can be uniquely determined from the coating peak amplitude, and this is independent to all other material parameters (diffusivity and thickness of both layers). On the other hand, the time duration before the peak is mostly related to the parameter $L_1^2/\alpha_1$ and also slightly to the parameter $e_1/e_2$ but not to the parameter $L_2^2/\alpha_2$; and the time duration after the peak is mostly to the parameter $L_2^2/\alpha_2$. Based on these observations, this method therefore can be configured to measure: (1) coating/film thermal effusivity with known substrate effusivity; (2) thermal effusivity of a bulk material (by bonding a calibrated film on the material surface); and (3) thermal diffusivity of a bulk plate material with known plate thickness (or vice versa). Both measurements (1) and (2) are validated here to have a measurement accuracy of <2% absolute errors. For (3), a detailed accuracy analysis was not performed here. These measurement capabilities may not only be used to determine average material properties but also for their two-dimensional distributions because the thermal imaging apparatus in FIG. 1 naturally obtains two-dimensional image data.

Figure 4:
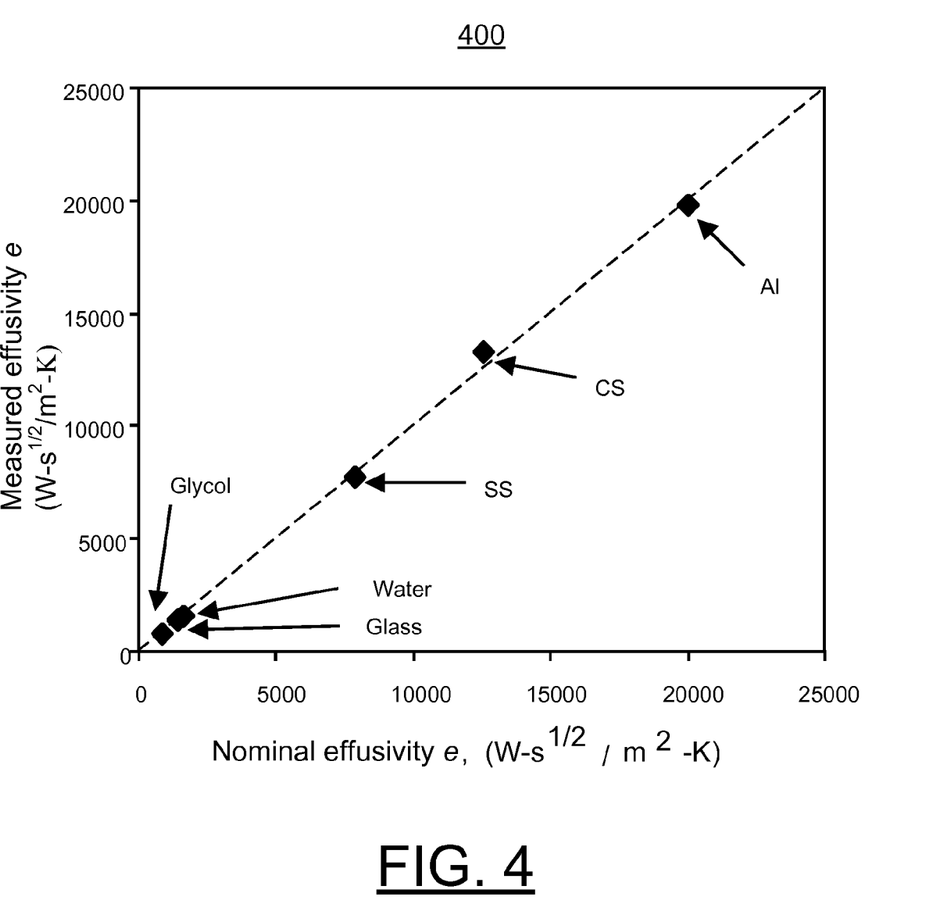
FIG. 4 is a chart illustrating comparison of predicted absolute thermal effusivity with nominal thermal effusivity values for various example materials in accordance with preferred embodiment.

Seven liquid and solid materials were tested; they are listed in TABLE 1. As seen in FIG. 4, the selected materials have a wide range of material properties (with a thermal conductivity ratio up to 580) that cover most commonly used engineering materials.

In FIG. 4, the predicted absolute thermal effusivities for all materials are compared with nominal values and in following Table 1. The prediction error is found to be <2%. The only exception was for the carbon steel material (it was not counted as a valid data point), which was because the surface of the sample was rough so a thermal resistance existed between the sample and electric tape.

The good measurement accuracy of <2% absolute errors for these materials validates the assumption that the electric tape has a constant thermal effusivity. It also serves as a proof that, when measuring unknown coating property with known substrate properties, the coating thermal effusivity measurement may achieve an accuracy of <2% absolute errors.

TABLE 1

| | Nominal values | | | | Measured values | |
|---|---|---|---|---|---|---|
| Material | p (g/cm$^3$) | c (J/kg-K) | k (W/m-K) | e (W-s$^{1/2}$/m$^2$-k) | e (W-s$^{1/2}$/m$^2$-k) | Δele (%) |
| Water (20° C.) | 0.998 | 4286 | 0.604 | 1607.8 | 1607.8 ± 2.86 | 0* |

TABLE 1-continued

| Material | Nominal values | | | | Measured values | |
| --- | --- | --- | --- | --- | --- | --- |
| | p (g/ cm³) | c (J/ kg-K) | k (W/ m-K) | e (W-s^{1/2}/ m²-k) | e (W-s^{1/2}/ m²-k) | Δe/e (%) |
| Ethylene Glycol (20° C.) | 1.113 | 2354 | 0.256 | 819.0 | 819.5 ± 4.99 | 0.06 |
| Borosilicate (pyrex) glass | 2.23 | 837 | 1.1 | 1432.9 | 1406.3 ± 2.84 | −1.86 |
| Stainless steel (309) | 8 | 500 | 15.6 | 7899.4 | 7771.4 ± 13.6 | −1.62 |
| Carbon steel (1080) | 7.8 | 470 | 43.0 | 12555 | 13315 ± 22.5 | 6.05^ |
| Aluminum (7895) | 2.8 | 960 | 149 | 20013 | 19815 ± 14.8 | −0.99 |

\* Water was used to calibrate the electric tape so it has no "measurement" error.
^Measured value was affected by sample surface roughness; it was not counted but listed for reference only.

Figure 5:
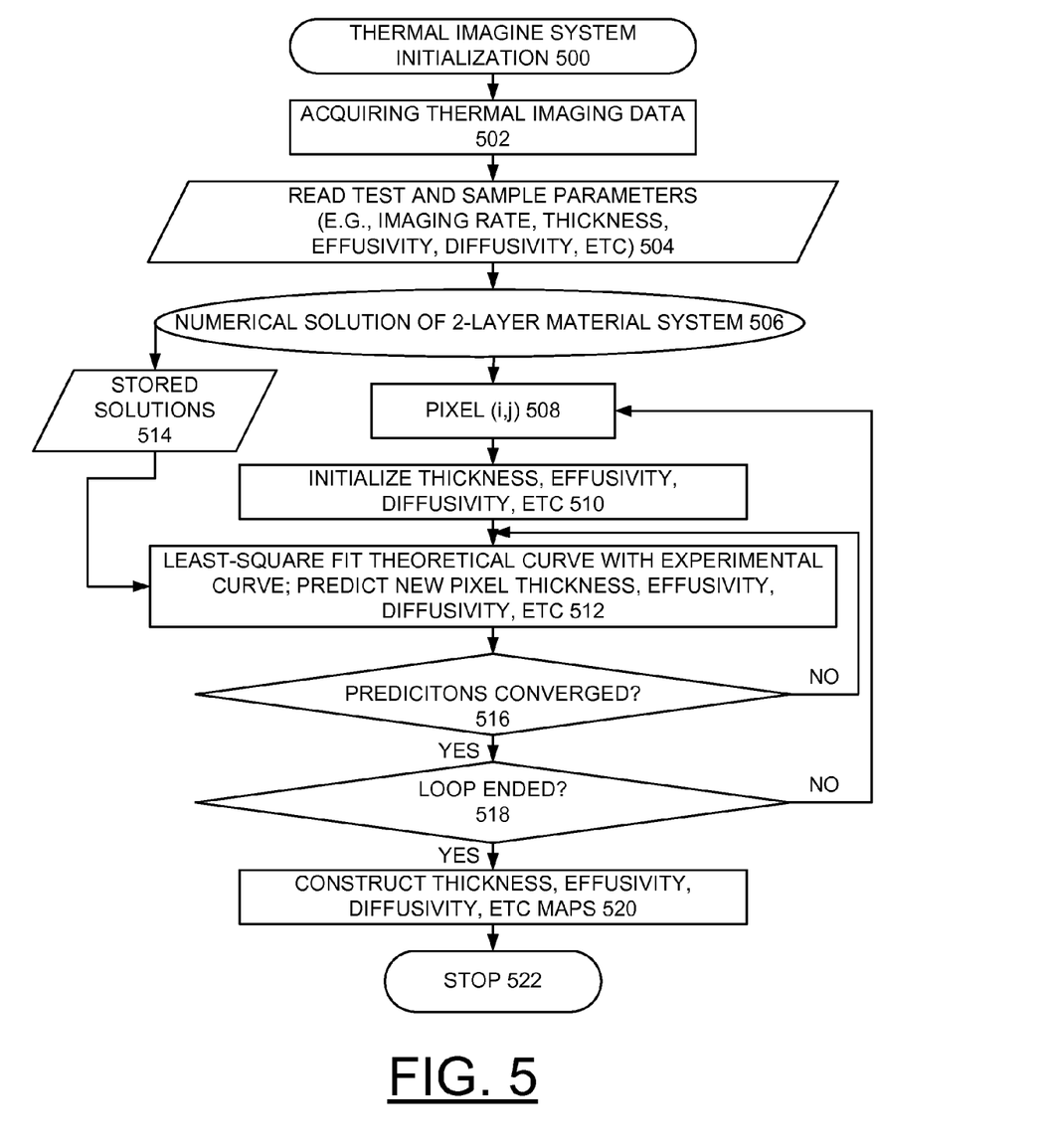
FIG. 5 is a flow chart illustrating exemplary steps for analyzing thermal imaging data in accordance with the preferred embodiment.

FIG. 5 illustrates a flow chart of the developed software for data processing, which is fully automated to simultaneously determine the distributions of these material thermal properties.

Referring to FIG. 5, there are shown exemplary steps for analyzing thermal imaging data in accordance with the preferred embodiment. In accordance with features of the invention, a general method and numerical algorithm are provided for automated analysis of thermal imaging data for multi-layer materials. It is based on a theoretical model of a multi-layer material system which is solved numerically, as disclosed in the above-identified U.S. Pat. No. 7,769,201. The Crank-Nicolson algorithm is used to discretize the governing equation with constant thermal properties and uniform spatial grids is expressed as:

$$\frac{T_j^{n+1} - T_j^n}{\Delta t} = \frac{\alpha}{2}\left[\frac{(T_{j+1}^{n+1} - 2T_j^{n+1} + T_{j-1}^{n+1}) + (T_{j+1}^n - 2T_j^n + T_{j-1}^n)}{(\Delta z)^2}\right] \quad (3)$$

where the superscript n denotes the time step and the subscript j denotes grid number. The Crack-Nicolson algorithm has $2^{nd}$-order accuracy in both time and space and, because it's an implicit algorithm, is unconditionally stable so grid size and time step can be arbitrarily chosen. In addition, because a 1D model is used in this method, the numerical solution matrix is tri-diagonal, so it can be easily and efficiently solved.

The Crank-Nicolson algorithm or scheme implemented in the accompanying software is formulated with variable time steps and nonuniform grid sizes in different material layers. The formulation also incorporates finite flash duration and volume heat absorption effects. The numerical formulation is derived based on the discretization of the multi-layer system which is provided from the input, for example, each layer can be discretized into tens to thousands of grids. The time steps are automatically chosen from the inputted experimental thermal-imaging data to be analyzed. The numerical formulation is then solved to provide numerical solutions of surface temperature based on the inputted layer dimension and thermal properties.

The numerical solutions are fitted with the experimental data by least-square minimization to determine unknown parameters in the multi-layer material system. Parameters in one or several layers can be determined simultaneously. For a two-layer coating/substrate system, the most interest parameters are the thickness, thermal conductivity, and absorption coefficient of the coating in the first layer. When a numerical result matches the experimental data (measured surface temperature decay from pulsed thermal imaging test), the correct parameters for the multi-layer material are determined. This least-square fitting process is carried out for each pixel within the 2D thermal imaging data, and the fitted parameters can be expressed in 2D images of the individual parameters. In order to save computation time, numerical solutions for unknown parameters within specified limiting ranges are calculated first and stored in computer memory. During the fitting process, these solutions are interpolated to obtain intermediate parameter values within the limiting ranges.

Referring now to FIG. 5, there are shown exemplary software steps for analyzing thermal imaging data for the two-layer material systems. Image data processing is fully automated to simultaneously determine the distributions and images of coating thickness, conductivity, and absorption coefficient. As indicated in a block 500, first initialization of the thermal imaging system is preformed and thermal imaging data is acquired as indicated in a block 502. Multiple test and sample parameters are read, for example, imaging rate, number of layers, thickness, conductivity, and the like, as indicated in a block 504. A numerical solution of the multi-layer material system is processed as indicated in a block 506. A pixel (i, j) loop is obtained as indicated in a block 508, then the pixel thickness, conductivity, and absorption are initialized as indicated in a block 510. As indicated in a block 512, a least-square fit of a theoretical curve obtained from stored solutions as indicated in a block 514 with an experimental curve is performed and new pixel thickness, conductivity, and absorption is predicted. As indicated in a decision block 516, it is determined whether the predictions converged. If not then a next least-squared fit is performed at block 512. When the predictions converged, then checking whether the loop ended as indicated in a decision block 518. When the loop has not ended, then a next pixel (i, j) loop is obtained at block 508 and the processing continues with the next pixel (i, j) loop. When the loop has ended, then thickness, conductivity, and absorption maps are constructed as indicated in a block 520. This completes the analysis of thermal imaging data for the two-layer coating/substrate material system as indicated in a block 522.

While the present invention has been described with reference to the details of the embodiments of the invention shown in the drawing, these details are not intended to limit the scope of the invention as claimed in the appended claims.

What is claimed is:
1. A method for implementing measurement of material thermal properties including measurement of thermal effusivity of a coating and/or film or a bulk material of uniform property comprising:
   providing an infrared camera,
   providing a data acquisition and processing computer coupled to the infrared camera for acquiring and processing thermal image data,
   providing a flash lamp providing an input of heat onto the surface of a two-layer sample;
   providing an optical filter covering the flash lamp for attenuating an entire infrared wavelength range of thermal images taken of the surface of a sample, providing said optical filter including a pair of glass plates enclosing a water layer; and performing a measurement solution to determine material thermal properties including thermal effusivity of the sample.

2. The method as recited in claim 1, includes providing two-layer sample, and measuring thermal effusivity of each of the two layers without requiring other material information.

3. The method as recited in claim 1, wherein the measurement solution to determine material thermal properties including thermal effusivity of the sample is represented by:

$$T_f(t) = Q \cdot f_1(e_1^2 t) \cdot f_3\left(\frac{e_1}{e_2}, \frac{\alpha_1}{L_1^2}, t\right), \quad (1)$$

$$T_f(t) = \frac{Q}{\rho_1 c_1 L_1 + \rho_2 c_2 L_2} \cdot f_4\left(\frac{e_1}{e_2}, \frac{\alpha_1}{L_1^2}, \frac{\alpha_2}{L_2^2}, t\right), \quad (2)$$

where $T_f(t)$ represents a front surface temperature, where t is time and Q is the total amount of absorbed energy (heat) on surface for the two-layer sample of materials of uniform properties with an instantaneous heat impulse for the cases of a semi-infinite and a finite substrate thickness material, respectively; where L represents sample thickness, e represents thermal effusivity and $\rho c$ represents heat capacity; where the subscripts 1 and 2 denote the first-layer or shallow layer material and a second-layer or deep layer material, respectively.

4. The method as recited in claim 1, wherein performing a measurement solution to determines material thermal properties including thermal effusivity of the sample includes providing a measurement accuracy of <2% absolute errors.

5. The method as recited in claim 1, wherein performing a measurement solution to determine material thermal properties including thermal effusivity of the sample includes measuring coating and/or film thermal effusivity with known substrate effusivity.

6. The method as recited in claim 1, wherein performing a measurement solution to determines material thermal properties including thermal effusivity of the sample includes measuring thermal diffusivity of a bulk plate material with known plate thickness.

7. A method for implementing measurement of material thermal properties including measurement of thermal effusivity of a coating and/or film or a bulk material of uniform property comprising:
providing an infrared camera,
providing a data acquisition and processing computer coupled to the infrared camera for acquiring and processing thermal image data,
providing a flash lamp providing an input of heat onto the surface of a two-layer sample;
providing an optical filter covering the flash lamp for attenuating an entire infrared wavelength range of thermal images taken of the surface of a sample; and
performing a measurement solution to determine material thermal properties including thermal effusivity of the sample includes measuring thermal effusivity of a bulk material by bonding a calibrated film on a material surface of the bulk material.

8. A system for implementing measurement of material thermal properties including measurement of thermal effusivity of a coating and/or film or a bulk material of uniform property comprising:
an infrared camera,
a data acquisition and processing computer coupled to the infrared camera for acquiring and processing thermal image data,
a flash lamp providing an input of heat onto the surface of a two-layer sample;
an optical filter covering the flash lamp for attenuating an entire infrared wavelength range of thermal images taken of the surface of a sample, said optical filter including a pair of glass plates enclosing a water layer; and
said data acquisition and processing computer performing a measurement solution to determine material thermal properties including thermal effusivity of the sample.

9. The system as recited in claim 8, wherein the sample includes a two-layer sample, and thermal effusivity of each of the two layers is measured without requiring other material information.

10. The system as recited in claim 9, wherein the measurement solution to determine material thermal properties including thermal effusivity of the sample is represented by:

$$T_f(t) = Q \cdot f_1(e_1^2 t) \cdot f_3\left(\frac{e_1}{e_2}, \frac{\alpha_1}{L_1^2}, t\right), \quad (1)$$

$$T_f(t) = \frac{Q}{\rho_1 c_1 L_1 + \rho_2 c_2 L_2} \cdot f_4\left(\frac{e_1}{e_2}, \frac{\alpha_1}{L_1^2}, \frac{\alpha_2}{L_2^2}, t\right), \quad (2)$$

where $T_f(t)$ represents a front surface temperature, where t is time and Q is the total amount of absorbed energy (heat) on surface for the two-layer sample of materials of uniform properties with an instantaneous heat impulse for the cases of a semi-infinite and a finite substrate thickness material, respectively; where L represents sample thickness, e represents thermal effusivity and $\rho c$ represents heat capacity; where the subscripts 1 and 2 denote the first-layer or shallow layer material and a second-layer or deep layer material, respectively.

11. The system as recited in claim 8, wherein said data acquisition and processing computer performing a measurement solution to determine material thermal properties including thermal effusivity of the sample provides a measurement accuracy of <2% absolute errors.

12. The system as recited in claim 8, wherein said data acquisition and processing computer performing a measurement solution to determine material thermal properties including thermal effusivity of the sample includes said data acquisition and processing computer measuring coating and/or film thermal effusivity with known substrate effusivity.

13. The system as recited in claim 8, wherein said data acquisition and processing computer performing a measurement solution to determine material thermal properties including thermal effusivity of the sample includes said data acquisition and processing computer measuring thermal effusivity of a bulk material by bonding a calibrated film on a material surface of the bulk material.

14. The system as recited in claim 8, wherein said data acquisition and processing computer performing a measurement solution to determine material thermal properties including thermal effusivity of the sample includes said data acquisition and processing computer measuring thermal diffusivity of a bulk plate material with known plate thickness.

* * * * *